United States Patent

Eckhardt et al.

Patent Number: 5,190,945
Date of Patent: Mar. 2, 1993

[54] AZINYLIMINODITHIETANES AND THEIR FUNGICIDAL AND NEMATOCIDAL METHODS OF USE

[75] Inventors: Wolfgang Eckhardt, Lörrach, Fed. Rep. of Germany; Urs Müller, Münchenstein, Switzerland

[73] Assignee: Ciba-Geigy Corporation, Ardsley, N.Y.

[21] Appl. No.: 794,537

[22] Filed: Nov. 19, 1991

Related U.S. Application Data

[62] Division of Ser. No. 641,032, Jan. 14, 1991, abandoned.

[30] Foreign Application Priority Data

Jan. 18, 1990 [CH] Switzerland ............ 163/90

[51] Int. Cl.⁵ ............... A61K 31/445; A61K 31/505; C07D 239/02; C07D 415/00
[52] U.S. Cl. ....................... 514/255; 514/256; 514/269; 514/272; 514/274; 514/275; 544/300; 544/316; 544/317; 544/319; 544/320; 544/327; 544/331; 544/333
[58] Field of Search ............... 544/300, 316, 320, 319, 544/331, 333, 317, 327; 514/256, 255, 269, 272, 275, 274

[56] References Cited

U.S. PATENT DOCUMENTS

| | | | |
|---|---|---|---|
| 3,928,382 | 12/1975 | Addor et al. | 549/89 |
| 3,997,668 | 12/1976 | Addor et al. | 514/363 |
| 4,009,279 | 2/1977 | Addor et al. | 514/430 |
| 4,144,339 | 3/1979 | Barreau et al. | 424/251 |
| 4,761,481 | 8/1988 | Hale et al. | 546/296 |
| 4,897,415 | 1/1990 | Hübl et al. | 514/430 |

FOREIGN PATENT DOCUMENTS 0310540 4/1989 European Pat. Off.

*Primary Examiner*—Nicholas S. Rizzo
*Assistant Examiner*—Matthew V. Grumbling
*Attorney, Agent, or Firm*—Edward McC. Roberts

[57] ABSTRACT

2-(Pyrimidyl or pyrazinyl)-imino-1,3-dithietanes

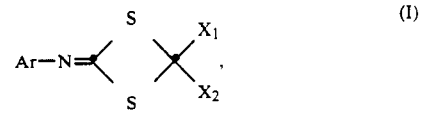

wherein Ar is one of the radicals

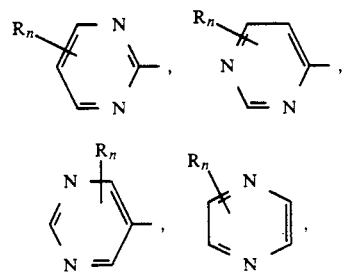

R is unsubstituted $C_1$-$C_3$alkyl or $C_1$-$C_3$alkyl which is substituted by halogen, $C_1$-$C_3$alkyl, $C_1$-$C_3$alkoxy, $C_1$-$C_3$alkylthio or cyano, independently of one another, or is unsubstituted or halo-substituted $C_3$-$C_7$alkenyl, unsubstituted or halo-substituted $C_3$-$C_7$alkynyl, or $C_3$-$C_5$cycloalkyl, $C_1$-$C_3$alkoxy, $C_1$-$C_3$alkylamino, nitro or halogen, n is a number from 0 to 3, $X_1$ and $X_2$ independently of each other are hydrogen or halogen, including the addition salts formed with acids of the formula $H^{\oplus}X^{\ominus}$ in which the anion $X^{\ominus}$ is $Cl^{\ominus}$, $Br^{\ominus}$, $I^{\ominus}$, $HSO_4-$, $H_2PO_4-$, $H_2PO_3-$, $NO_3-$, $CH_3COO^{\ominus}$, $CH_2ClCOO-$, $CF_3COO-$, $HOCH_2COO-$, $CH_3CH(OH)COO^{\ominus}$, $HOOCCOO^{\ominus}$, $HOOCCH_2COO^{\ominus}$, $HOOCCH=CHCOO^{\ominus}$,

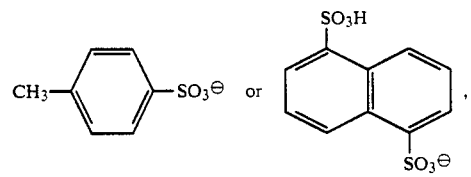

a process for the preparation of the compounds of formula I, and novel intermediates of the preparation process are described.

The compounds of formula I have nematicidal and fungicidal properties. Nematicidal and fungicidal compositions that contain at least one compound of formula I as active ingredient, and also methods of using the compounds and the compositions in the control of nematodes and fungi, are described.

14 Claims, No Drawings

AZINYLIMINODITHIETANES AND THEIR FUNGICIDAL AND NEMATOCIDAL METHODS OF USE

This is a division of Ser. No. 641,032 filed Jan. 14, 1991, now abandoned.

The present invention relates to novel 2-(pyrimidyl or pyrazinyl)-imino-1,3-dithietanes, to the preparation thereof, and to nematicidal compositions that contain at least one of those compounds as active ingredient. The invention relates also to novel intermediates of the process for the preparation of the compounds, to the use thereof, and to compositions for controlling nematodes and fungi, especially plant-destructive nematodes and fungi.

The invention relates to 2-(pyrimidyl or pyrazinyl)-imino-1,3-dithietanes of formula I

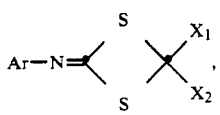

wherein
Ar is one of the radicals

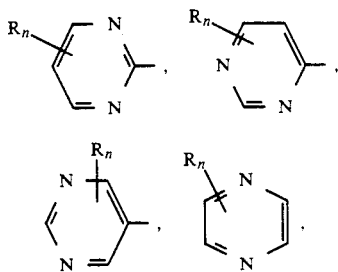

R is unsubstituted $C_1$–$C_3$alkyl or $C_1$–$C_3$alkyl which is substituted by halogen, $C_1$–$C_3$alkyl, $C_1$–$C_3$alkoxy, $C_1$–$C_3$alkylthio or cyano, independently of one another, or is unsubstituted or halo-substituted $C_3$–$C_7$alkenyl, unsubstituted or halo-substituted $C_3$–$C_7$alkynyl, or $C_3$–$C_5$cycloalkyl, $C_1$–$C_3$alkoxy, $C_1$–$C_3$alkylthio, di-$C_1$–$C_3$alkylamino, nitro or halogen, n is a number from 0 to 3, $X_1$ and $X_2$ independently of each other are hydrogen or halogen, including the addition salts formed with acids of the formula $H^\oplus X^\ominus$ in which the anion $X^\ominus$ is $Cl^\ominus$, $Br^\ominus$, $I^\ominus$, $HSO_4^-$, $H_2PO_4^-$, $H_2PO_3^-$, $NO_3^-$, $CH_3COO^\ominus$, $CH_2ClCOO^-$, $CF_3COO^-$, $HOCH_2COO^-$, $CH_3CH(OH)COO^\ominus$, $HOOCCOO^\ominus$, $HOOCCH_2COO^\ominus$, $HOOCCH=CHCOO^\ominus$,

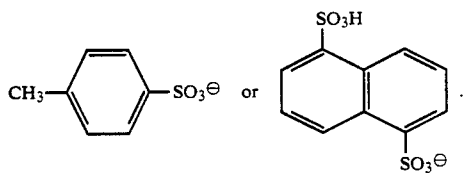

Alkyl as an independent radical and as part of another group, such as alkoxy, alkylthio or dialkylamino, shall be understood as including the methyl and ethyl groups and also normal propyl and isopropyl. Halo-substituted alkyl is a mono- to per-halogenated alkyl radical, for example $CHCl_2$, $CH_2F$, $CCl_3$, $CH_2Cl$, $CHFCH_2$, $CH_2CH_2Br$, $CF_2CF_3$, $C_2Cl_5$, $CH_2Br$, $CHBrCl$, etc.. An example of alkylthio is ethylthio. Alkenyl is, for example, propenyl-(1), allyl, butenyl-(1), butenyl-(2) or butenyl-(3), and also chains having several double bonds. Alkynyl is, for example, propynyl-(2), butynyl-(1), butynyl-(2), pentynyl-(4), etc.. Halogen is fluorine, chlorine, bromine or iodine, preferably chlorine.

Examples of salt-forming acids are, of the inorganic acids: hydrohalic acids, such as hydrochloric acid, hydrobromic acid or hydriodic acid, and also sulfurous acid, sulfuric acid, phosphoric acid, phosphorous acid and nitric acid, and of the organic acids: acetic acid, trifluoroacetic acid, monochloroacetic acid, glycolic acid, succinic acid, oxalic acid, maleic acid, fumaric acid, p-toluenesulfonic acid and naphthalene-1,5-disulfonic acid.

Salts of 2-(2-pyridylimino)-1,3-thietane having nematicidal activity are already known from EP-A-310540, but in the control of harmful nematodes they are unable fully to satisfy the demands made of them.

With the provision of the compounds of formula I according to the invention, it is now possible to make a valuable contribution to controlling plant nematodes and fungi which cause considerable agricultural damage to plants. In this manner, losses in yield of cultivated plants, for example potatoes, cereals, beet crops, rape, cabbage, tobacco, soybeans, cotton, maize, rice and vegetables, and also damage caused in tree nurseries and to ornamentals can be inhibited over a prolonged period. The compounds according to the invention are distinguished especially by the fact that they effectively control soil nematodes that parasitise roots, for example nematodes of the genera Heterodera and Globodera (cystogenic nematodes), Meloidogyne (root-knot nematodes) and also of the genera Radopholus, Pratylenchus, Tylenchulus, Longidorus, Trichodorus and Xiphinema. The nematode genera Ditylenchus (stem parasites), Aphelenchoides (leaf nematodes) and Anguina (blossom nematodes) can also be effectively controlled with the compounds according to the invention.

Preferably, the compounds of formula I are used for successfully controlling especially harmful nematode species of the genus Meloidogyne, for example *Meloidogyne incognita*, of the genus Heterodera, for example *Heterodera glycines* (soybean cyst nematode), and of the genus Globodera, for example *Globodera rostochiensis* (potato cyst nematode), as well as representatives of migrating endoparasites, for example *Pratylenchus penetrans* or *Radopholus similis*, and representatives of ectoparasites, for example Trichodorus spp. and Xiphinema spp..

Preferably, the compounds of formula I are likewise used for successfully controlling especially harmful fungi, for example Ascomycetes, such as *Erysiphe gramini*, Fungi imperfecti, such as *Botrytis cinerea*, and *Cercospora beticola.*

To control plant nematodes and soil fungi and for the preservation of plant health, the novel compounds may be used curatively, preventively or systemically. They have a broad spectrum of activity against the various nematode and soil fungus species and therefore meet the requirements made of them in practice. The nematicidal and fungicidal mode of action of the compounds of the invention is coupled in advantageous manner with a low phytotoxicity, whereby the generally desirable reduction of harm to the environment is especially accommodated.

A preferred sub-group comprises compounds of formula I wherein R is methyl, methoxy, methylthio or chlorine, n is a number from 0 to 2, and $X_1$ and $X_2$ independently of each other are hydrogen or fluorine.

Of the above-mentioned compounds, special preference is given on account of their nematicidal activity to those compounds wherein R is methyl, methoxy or methylthio, n is 0 or 1, and $X_1$ and $X_2$ are hydrogen.

Of those compounds, special mention should be made of those of formulae Ia, Ib, Ic and Id

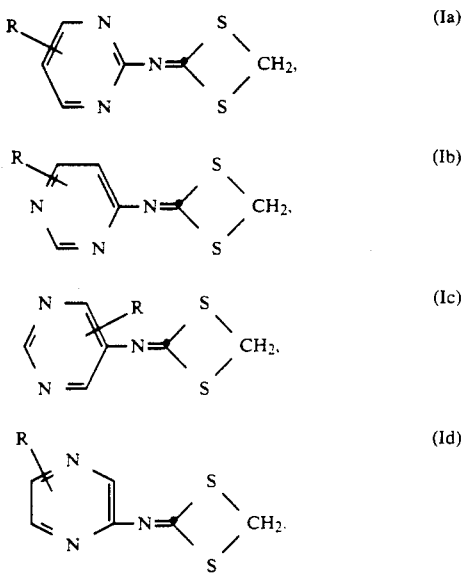

Of the compounds of formula Ia, special mention should be made of 2-(2-pyrimidyl)-imino-1,3-dithietane.

Of the compounds of formula Ib, mention should be made of 2-(4-pyrimidyl)-imino-1,3-dithietane.

Similarly, of the compounds of formula Ic, special mention may be made of 2-(5-pyrimidyl)-imino-1,3-dithietane.

Finally, of the compounds of formula Id, 2-(2-pyrazinyl)-imino-1,3-dithietane is of importance.

According to the invention, compounds of formula I are prepared by converting a pyrimidyl- or pyrazinyl-amine of formula II into an adduct of formula III with carbon disulfide and with a base B, with or without a solvent, at from $-10°$ to $50°$ C.

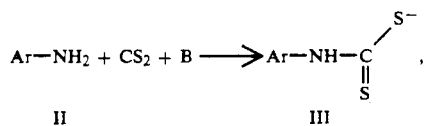

converting that adduct into the reaction product of formula I with a dibromomethane derivative of formula IV or with the corresponding diiodo derivative and with a base, with or without a solvent, at from $-10°$ to $100°$ C.

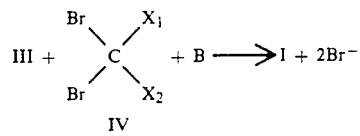

and isolating that reaction product or converting it into the addition salt $I.H^{\oplus}X^{\ominus}$ with an acid of the formula $H^{\oplus}X^{\ominus}$, the radicals Ar, $X_1$, $X_2$ and $X^{\ominus}$ being as defined under formula I and B being a hydroxide, a hydride or a carbonate of an alkali metal or an alkaline earth metal, or a tertiary amine. The present invention also includes that process.

The starting materials of formulae II and IV are generally known and can be prepared by known processes.

According to a preferred form of the process according to the invention, the preparation of the adduct of formula III is carried out in a solvent at from 0° to 40° C., and the reaction of that adduct with the dibromomethane derivative of formula IV is carried out in a solvent at from 0° to 80° C.

This form is preferred when B is a trialkylamine or a hydride, a hydroxide or a carbonate of an alkali metal or an alkaline earth metal.

Solvents or diluents suitable for the preparation of the active ingredients according to the invention are, for example, alcohols, such as methanol, ethanol, isopropanol or butanol; N,N-dialkylated amides, such as dimethylformamide; dimethyl sulfoxide; ethers and ethereal compounds, such as dialkyl ethers (diethyl ether, diisopropyl ether, tert.-butyl methyl ether, etc.), anisole, dioxane, tetrahydrofuran; aliphatic and aromatic hydrocarbons, such as benzene, toluene, petroleum ether; halogenated hydrocarbons, such as chlorobenzene, methylene chloride, chloroform, ethylene chloride, carbon tetrachloride, tetrachloroethylene; nitriles, such as acetonitrile, propionitrile; ketones, such as acetone, diethyl ketone, methyl ethyl ketone; and also water and, very generally, mixtures of such solvents with one another.

Suitable bases are organic and inorganic bases; for example preferably tertiary amines, such as trialkylamines (trimethylamine, triethylamine, tripropylamine, etc.) as well as oxides, hydroxides, carbonates and hydrogen carbonates of alkali metals and alkaline earth metals (e.g. CaO, BaO, NaOH, KOH, Ca(OH)$_2$, KHCO$_3$, NaHCO$_3$, Ca(HCO$_3$)$_2$, K$_2$CO$_3$, Na$_2$CO$_3$, etc.), and also acetates, such as CH$_3$COONa or CH$_3$COOK. Furthermore, suitable bases are also alkali metal alcoholates, for example sodium ethanolate, sodium propanolate, potassium tert.-butanolate or sodium ethanolate, and also alkali metal hydrides, for example sodium hydride.

The invention relates also to compositions, for controlling plant-destructive nematodes and for protecting plants from attack by nematodes, that contain the compounds of formula I.

In addition, the present invention also includes the preparation of nematicidal and fungicidal compositions, which comprises homogeneously mixing compounds of formula I with one or more of the carriers and adjuvants described herein. Also included is a method of treating plants, which comprises applying thereto the compounds of formula I or the novel compositions.

A preferred method of applying a compound of formula I or a nematicidal composition containing at least one of those compounds, is incorporation into the soil, which comprises treating the locus of the plants with a liquid or solid formulation.

The compounds of formula I can, however, also be applied to seeds (dressing/coating) either by impregnating the seeds with a liquid formulation of the active ingredient or by coating them with a solid formulation. In special cases, other methods of application are also possible, for example selective treatment of the plant stems, buds or leaves.

The compounds of formula I are normally applied in the form of compositions and can be applied to the crop area or plant to be treated, simultaneously or in succession, with further compounds. These further compounds can also include other substances applied in agriculture which are used to increase production by promoting the growth of useful plants, such as fertilisers, herbicides, insecticides, fungicides, molluscicides etc., or may be mixtures of several of these preparations, if desired together with further carriers, surfactants or other application-promoting adjuvants customarily employed in the art of formulation.

Suitable carriers and adjuvants can be solid or liquid and correspond to the substances ordinarily employed in formulation technology, e.g. natural or regenerated mineral substances, solvents, dispersants, wetting agents, tackifiers, thickeners, binders or fertilisers.

The compounds of formula I are used in unmodified form or, preferably, together with at least one adjuvant or the adjuvants conventionally employed in the art of formulation, respectively. They are formulated in known manner e.g. into emulsifiable concentrates, directly sprayable or dilutable solutions, dilute emulsions, wettable powders, soluble powders, dusts, granulates, and also encapsulations in e.g. polymer substances. As with the nature of the compositions, the methods of application, such as spraying, dusting, scattering or pouring, are chosen in accordance with the intended objectives and the prevailing circumstances. Advantageous rates of application are normally from 300 g to 6 kg of active ingredient (a.i.) per hectare; preferably from 0.3 to 2 kg a.i./ha.

The formulations, i.e. the compositions, preparations or mixtures containing the compound (active ingredient) of formula I and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such an N-methyl-2-pyrrolidone, dimethyl sulfoxide or dimethylformamide, as well as vegetable oils or epoxidised vegetable oils, such as epoxidised coconut oil or soybean oil; or water.

The solid carriers used, e.g. for dusts and dispersible powders, are normally natural mineral filers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are, for example, calcite or sand. In addition, a great number of pregranulated materials of inorganic or organic nature can be used, e.g. especially dolomite or pulverised plant residues.

Depending on the nature of the compound of formula I to be formulated, suitable surface-active compounds are non-ionic, cationic and/or anionic surfactants having good emulsifying, dispersing and wetting properties. The term "surfactants" will also be understood as comprising mixtures of surfactants.

Both so-called water-soluble soaps and also water-soluble synthetic surface-active compounds are suitable anionic surfactants.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tallow oil. Mention may also be made of fatty acid methyllaurin salts and modified and unmodified phospholipids.

More frequently, however, so-called synthetic surfactants are used, especially fatty sulfonates, fatty sulfates, sulfonated benzimidazole derivatives or alkylsulfonates.

The fatty alcohol sulfonates or sulfates are usually in the form of alkali metal salts, alkaline earth metal salts or unsubstituted or substituted ammonium salts and contain a $C_8$–$C_{22}$alkyl radical, which also includes the alkyl moiety of acyl radicals, e.g. the sodium or calcium salt of lignosulfonic acid, of dodecylsulfate or of a mixture of fatty alcohol sulfates obtained from natural fatty acids. These compounds also comprise the salts of sulfated and sulfonated fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a condensate of naphthalenesulfonic acid and formaldehyde.

Also suitable are corresponding phosphates, e.g. salts of the phosphoric acid ester of an adduct of p-nonylphenol with 4 to 14 moles of ethylene oxide.

Non-ionic surfactants are preferably polyglycol ether derivatives of aliphatic or cycloaliphatic alcohols, saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethyleneethanol, polyethylene glycol and octylphenoxypolyethoxyethanol.

Fatty acid esters of polyoxyethylene sorbitan, e.g. polyoxyethylene sorbitan trioleate, are also suitable non-ionic surfactants.

Cationic surfactants are preferably quaternary ammonium salts which contain, as N-substituent, at least one $C_8$-$C_{22}$alkyl radical and, as further substituents, unsubstituted or halogenated lower alkyl, benzyl or hydroxy-lower alkyl radicals. The salts are preferably in the form of halides, methyl sulfates or ethyl sulfates, e.g. stearyltrimethylammonium chloride or benzyldi(2-chloroethyl)ethylammonium bromide.

The surfactants customarily employed in the art of formulation are described inter alia in the following publications:

"McCutcheon's Detergents and Emulsifiers Annual", MC Publishing Corp., Ridgewood, N.J., 1979; Dr. Helmut Stache, "Tensid Taschenbuch", Carl Hanser Verlag, Munich/Vienna.

The agrochemical compositions usually contain 0.1 to 99% by weight, preferably 0.1 to 95% by weight, of a compound of formula I, 99.9 to 1% by weight, preferably 99.8 to 5% by weight, of a solid or liquid adjuvant, and 0 to 25% by weight, preferably 0.1 to 25% by weight, of a surfactant.

Whereas commercial products will preferably be formulated as concentrates, the end user will normally employ dilute formulations.

The compositions may also contain further auxiliaries such as stabilisers, antifoams, viscosity regulators, binders, tackifiers as well as fertilisers or other active ingredients for obtaining special effects.

The present invention relates also to such agrochemical compositions.

The following Examples illustrate the invention in greater detail but do not limit the invention.

1. PREPARATION EXAMPLES 2-(5-Pyrimidylimino)-1,3-dithietane (Compound 1.1)

23.4 g (0.232 mol) of triethylamine are added dropwise to a ready-prepared solution of 20 g (0.211 mol) of 5-aminopyrimidine and 12.7 ml (0.211 mol) of carbon disulfide in 50 ml of ethyl alcohol. The reaction mixture is then stirred for 15 hours at 70° C. and the resulting suspension is filtered off. Drying yields 10 g of carbon disulfide adduct. The filtrate is concentrated by evaporation, yielding a further 27 g of the intermediate as the residue.

A mixture of 41.9 g (0.241 mol) of dibromomethane and 3.7 g (0.037 mol) of triethylamine in 20 ml of dimethylformamide is added dropwise at 25° C. with stirring to 10 g (0.037 mol) of the intermediate in 40 ml of dimethylformamide. The reaction mixture is stirred at 25° C. for 20 hours and then poured onto ice-water and extracted with diethyl ether. The combined diethyl ether extracts are extracted three times with 100 ml of water each time, dried over sodium sulfate, filtered and concentrated by evaporation. The crude product is purified over a silica gel flash column with ethyl acetate/hexane (2/1), yielding 2.7 g (40% of the theoretical yield) of product having a melting point of 97°-99° C.

2-(5-Pyrimidylimino)-1,3-dithietane hydrochloride (Compound 1.2)

Dry HCl gas is introduced at 0°-10° C. over a period of half an hour into a solution of 0.5 g (2.732 mmol) of 2-(5-pyrimidylimino)-1,3-dithietane in 50 ml of diethyl ether. The resulting product is filtered off, washed with diethyl ether and dried, yielding 0.5 g (83.4% of the theoretical yield) of product having a melting point (decomp.) of 150° C. and above.

The compounds listed in the following Tables 1 to 4 can be prepared analogously to the above Examples.

TABLE 1

2-(5-Pyrimidyl)-imino-1,3-dithietanes

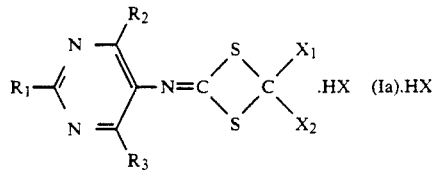

| Comp No. | $R_1$ | $R_2$ | $R_3$ | $X_1$ | $X_2$ | HX | Physical data |
|---|---|---|---|---|---|---|---|
| 1.1 | H | H | H | H | H | — | m.p. 97-99° C. |
| 1.2 | H | H | H | H | H | HCl | m.p. >150° C. (decomp.) |
| 1.3 | H | H | H | H | H | $H_2SO_4$ | m.p. >110° C. (decomp.) |
| 1.4 | H | H | H | H | H | HBR | |
| 1.5 | H | H | H | H | H | HI | |
| 1.6 | H | H | H | H | H | $HNO_3$ | |
| 1.7 | H | H | H | H | H | $H_2SO_3$ | |
| 1.8 | H | H | H | H | H | $H_3PO_4$ | |
| 1.9 | H | H | H | H | H | $CH_3COOH$ | |
| 1.10 | H | H | H | H | H | $(COOH)_2$ | |
| 1.11 | H | H | H | H | H | $ClCH_2COOH$ | |
| 1.12 | H | H | H | H | H | $HOCH_2COOH$ | |
| 1.13 | H | H | H | H | H | $CH_2(COOH)_2$ | |
| 1.14 | H | H | H | H | H | CH—COOH ‖ CH—COOH | |

TABLE 1-continued 2-(5-Pyrimidyl)-imino-1,3-dithietanes

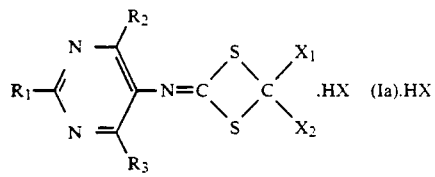

.HX  (Ia).HX

| Comp No. | $R_1$ | $R_2$ | $R_3$ | $X_1$ | $X_2$ | HX | Physical data |
|---|---|---|---|---|---|---|---|
| 1.15 | H | H | H | H | H | CH₃—⟨benzene⟩—SO₃H | |
| 1.16 | H | H | H | H | H | naphthalene-1,5-disulfonic acid (SO₃H, SO₃H) | |
| 1.17 | CH₃— | H | H | H | H | — | |
| 1.18 | CH₃ | H | H | H | H | HCl | |
| 1.19 | CH₃ | H | H | H | H | H₂SO₄ | |
| 1.20 | H | H | H | F | F | — | |
| 1.21 | H | H | H | Cl | Cl | — | |
| 1.22 | CH₃ | H | H | F | F | — | |

TABLE 2

2-(4-Pyrimidyl)-imino-1,3-dithietanes

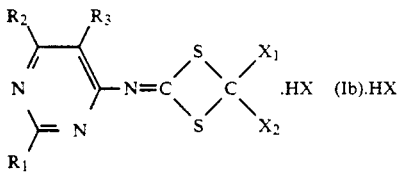

.HX  (Ib).HX

| Comp No. | $R_1$ | $R_2$ | $R_3$ | $X_1$ | $X_2$ | HX | Physical data |
|---|---|---|---|---|---|---|---|
| 2.1 | H | H | H | H | H | — | m.p. 153–155° C. |
| 2.2 | H | H | H | H | H | HCl | |
| 2.3 | H | H | H | H | H | H₂SO₄ | |
| 2.4 | H | H | H | H | H | CH₃COOH | |
| 2.5 | H | H | H | H | H | CH₃—⟨benzene⟩—SO₃H | |
| 2.6 | CH₃ | CH₃ | H | H | H | — | |
| 2.7 | CH₃ | CH₃ | H | H | H | HCl | |
| 2.8 | CH₃ | CH₃ | H | H | H | H₂SO₄ | |
| 2.9 | CH₃S | Cl | H | H | H | — | |
| 2.10 | CH₃S | Cl | H | H | H | HCl | |
| 2.11 | CH₃S | Cl | H | H | H | H₂SO₄ | |
| 2.12 | H | H | H | F | F | — | |
| 2.13 | H | H | H | Cl | Cl | — | |
| 2.14 | CH₃S | H | Cl | F | F | — | |
| 2.15 | CH₃O | H | CH₃O | F | F | — | |

TABLE 3

2-(2-Pyrimidyl)-imino-1,3-dithietanes

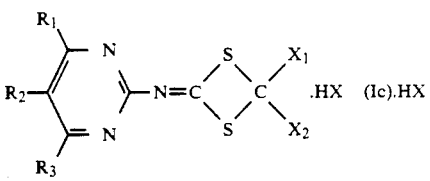

| Comp. No. | $R_1$ | $R_2$ | $R_3$ | $X_1$ | $X_2$ | HX | Physical data |
|---|---|---|---|---|---|---|---|
| 3.1 | H | H | H | H | H | — | m.p.: 173–175° C. |
| 3.2 | H | H | H | H | H | HCl | |
| 3.3 | H | H | H | H | H | $H_2SO_4$ | |
| 3.4 | H | H | H | H | H | $CH_3COOH$ | |
| 3.5 | H | H | H | H | H | $HNO_3$ | |
| 3.6 | H | H | H | H | H | $CH_3$-C$_6$H$_4$-$SO_3H$ | |
| 3.7 | H | Br | H | H | H | — | |
| 3.8 | H | Br | H | H | H | HCl | |
| 3.9 | H | Br | H | H | H | $H_2SO_4$ | |
| 3.10 | H | $CH_3$ | H | H | H | — | m.p. 102–103° C. |
| 3.11 | H | $CH_3$ | H | H | H | HCl | |
| 3.12 | $CH_3$ | H | $CH_3$ | H | H | — | |
| 3.13 | $CH_3$ | H | $CH_3$ | H | H | HCl | |
| 3.14 | $CH_3$ | H | $CH_3$ | H | H | $H_2SO_4$ | |
| 3.15 | $CH_3$ | H | cyclopropyl | H | H | — | |
| 3.16 | $CH_3$ | H | cyclopropyl | H | H | HCl | |
| 3.17 | $CH_3$ | H | cyclopropyl | H | H | $H_2SO_4$ | |
| 3.18 | $CH_3$ | H | H | H | H | — | |
| 3.19 | $CH_3$ | H | H | H | H | HCl | |
| 3.20 | $CH_3$ | H | H | H | H | $H_2SO_4$ | |
| 3.21 | H | $NO_2$ | H | H | H | — | |
| 3.22 | H | $NO_2$ | H | H | H | HCl | |
| 3.23 | H | $NO_2$ | H | H | H | $H_2SO_4$ | |
| 3.24 | H | H | H | F | F | — | |
| 3.25 | H | H | H | Cl | Cl | — | |
| 3.26 | H | Br | H | F | F | — | |
| 3.27 | H | $CH_3$ | H | F | F | — | |
| 3.28 | $CH_3$ | H | $CH_3$ | F | F | — | |
| 3.29 | $CH_3$ | H | cyclopropyl | F | F | — | |
| 3.30 | H | $NO_2$ | H | F | F | — | |
| 3.31 | Cl | H | $CH_3$ | H | H | — | |
| 3.32 | Cl | H | $CH_3$ | H | H | HCl | |
| 3.33 | Cl | H | $CH_3$ | H | H | $H_2SO_4$ | |
| 3.34 | Cl | H | $CH_3$ | F | F | — | |
| 3.35 | Cl | H | Cl | H | H | — | |
| 3.36 | $CH_3$ | H | $OCH_3$ | H | H | — | |
| 3.37 | $CH_3$ | H | $OCH_3$ | H | H | HCl | |
| 3.38 | $CH_3$ | H | $OCH_3$ | H | H | $H_2SO_4$ | |

TABLE 4

2-(2-Pyrazinyl)-imino-1,3-dithietanes

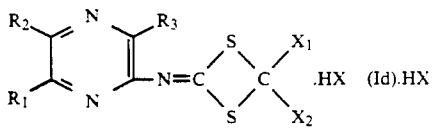

.HX    (Id).HX

| Comp No. | $R_1$ | $R_2$ | $R_3$ | $X_1$ | $X_2$ | HX | Physical data |
|---|---|---|---|---|---|---|---|
| 4.1 | H | H | H | H | H | — | m.p. 154–156° C. |
| 4.2 | H | H | H | H | H | HCl | m.p. 162–165° C. |
| 4.3 | H | H | H | H | H | $H_2SO_4$ | m.p. 158–159° C. |
| 4.4 | H | H | H | H | H | $CH_3\text{-}C_6H_4\text{-}SO_3H$ | |
| 4.5 | H | H | H | F | F | — | |
| 4.6 | H | H | H | F | F | HCl | |
| 4.7 | H | H | H | F | F | $H_2SO_4$ | |
| 4.8 | $CH_3$ | H | H | H | H | — | |
| 4.9 | $CH_3$ | $CH_3$ | H | H | H | — | |
| 4.10 | $CH_3$ | $CH_3$ | H | F | F | — | |
| 4.11 | H | H | $CH_3$ | H | H | — | |

2. FORMULATION EXAMPLES FOR LIQUID ACTIVE INGREDIENTS OF FORMULA I (THROUGHOUT, PERCENTAGES ARE BY WEIGHT)

2.1 Emulsifiable Concentrates

| | a) | b) | c) |
|---|---|---|---|
| a compound of Tables 1 to 4 | 25% | 40% | 50% |
| calcium dodecyl benzenesulfonate | 5% | 8% | 6% |
| castor oil polyethylene glycol ether (36 moles of ethylene oxide) | 5% | — | — |
| tributylphenol polyethylene glycol ether (30 moles of ethylene oxide) | — | — | 12% |
| cyclohexanone | — | 15% | 20% |
| xylene mixture | 65% | 25% | 20% |

Emulsions of any desired concentration can be produced from such concentrates by dilution with water.

2.2 Solutions

| | a) | b) | c) | d) |
|---|---|---|---|---|
| a compound of Tables 1 to 4 | 80% | 10% | 5% | 95% |
| ethylene glycol monomethyl ether | 20% | — | — | — |
| polyethylene glycol (mol. wt. 400) | — | 70% | — | — |
| N-methyl-2-pyrrolidone | — | 20% | — | — |
| epoxidised coconut oil | — | — | 1% | 5% |
| petroleum fraction (boiling range 160–190° C.) | — | — | 94% | — |

These solutions are suitable for application in the form of microdrops.

2.3 Granulates

| | a) | b) |
|---|---|---|
| a compound of Tables 1 to 4 | 5% | 10% |
| kaolin | 94% | — |
| highly dispersed silicic acid | 1% | — |
| attapulgite | — | 90% |

The active ingredient is dissolved in methylene chloride, the solution is sprayed onto the carrier, and the solvent is subsequently evaporated off in vacuo.

2.4 Dusts

| | a) | b) |
|---|---|---|
| a compound of Tables 1 to 4 | 2% | 5% |
| highly dispersed silicic acid | 1% | 5% |
| talcum | 97% | — |
| kaolin | — | 90% |

Ready-for-use dusts are obtained by intimately mixing the carriers with the active ingredient.

FORMULATION EXAMPLES FOR SOLID ACTIVE INGREDIENTS OF FORMULA I (THROUGHOUT, PERCENTAGES ARE BY WEIGHT)

2.5 Wettable Powders

| | a) | b) | c) |
|---|---|---|---|
| a compound of Tables 1 to 4 | 25% | 50% | 75% |
| sodium lignosulfonate | 5% | 5% | — |
| sodium lauryl sulfate | 3% | — | 5% |
| sodium diisobutyl naphthalenesulfonate | — | 6% | 10% |
| octylphenol polyethylene glycol ether (7–8 moles of ethylene oxide) | — | 2% | — |
| highly dispersed silicic acid | 5% | 10% | 10% |
| kaolin | 62% | 27% | — |

The active ingredient is thoroughly mixed with the adjuvants and the mixture is thoroughly ground in a suitable mill, affording wettable powders which can be diluted with water to give suspensions of the desired concentration.

2.6 Emulsifiable Concentrate

| | |
|---|---|
| a compound of Tables 1 to 4 | 10% |
| octylphenol polyethylene glycol ether | 3% |

-continued

| | |
|---|---|
| (4–5 moles of ethylene oxide) | |
| calcium dodecyl benzenesulfonate | 3% |
| castor oil polyglycol ether | 4% |
| (35 moles of ethylene oxide) | |
| cyclohexanone | 30% |
| xylene mixture | 50% |

Emulsions of any required concentration can be obtained from this concentrate by dilution with water.

2.7 Dusts

| | a) | b) |
|---|---|---|
| a compound of Tables 1 to 4 | 5% | 8% |
| talcum | 95% | — |
| kaolin | — | 92% |

Ready-for-use dusts are obtained by mixing the active ingredient with the carriers and grinding the mixture in a suitable mill.

2.8 Extruder Granulate

| | |
|---|---|
| a compound of Tables 1 to 4 | 10% |
| sodium lignosulfonate | 2% |
| carboxymethylcellulose | 1% |
| kaolin | 87% |

The active ingredient is mixed and ground with the adjuvants, and the mixture is moistened with water. The mixture is extruded and then dried in a stream of air.

2.9 Coated Granulate

| | |
|---|---|
| a compound of Tables 1 to 4 | 3% |
| polyethylene glycol (mol. wt. 200) | 3% |
| kaolin | 94% |

The finely ground active ingredient is uniformly applied, in a mixer, to the kaolin moistened with polyethylene glycol. Non-dusty coated granulates are obtained in this manner.

2.10 Suspension Concentrate

| | |
|---|---|
| a compound of Tables 1 to 4 | 40% |
| ethylene glycol | 10% |
| nonylphenol polyethylene glycol ether | 6% |
| (15 moles of ethylene oxide) | |
| sodium lignosulfonate | 10% |
| carboxymethylcellulose | 1% |
| 37% aqueous formaldehyde solution | 0.2% |
| silicone oil in the form of a 75% | 0.8% |
| aqueous emulsion | |
| water | 32% |

The finely ground active ingredient is intimately mixed with the adjuvants, giving a suspension concentrate from which suspensions of any desired concentration can be obtained by dilution with water.

2. BIOLOGICAL EXAMPLES 2.1 Action Against *Meloidogyne incognita* on Tomato Plants Eggs of *Meloidogyne incognita* are mixed into sand. This mixture is then put into 200 ml clay pots (5000 eggs per pot). On the same day a three-week-old tomato plant is planted in each pot and the formulated test compound is introduced into the pots by drench application (0.0006% of active ingredient, based on the volume of the soil). The potted plants are then placed in a greenhouse at a temperature of $26° \pm 1°$ C. and a relative humidity of 60%. After 4 weeks, evaluation is made by examining the plants for root-knot formation in accordance with the so-called Root-Knot Index.

Compounds of Tables 1–4 exhibit activity against *Meloidogyne incognita* by reducing root-knot formation. On the other hand, untreated and infected control plants exhibit severe root-knot formation ($=100\%$). Compounds nos. 1.1, 1.2, 1.3, 3.1 and 4.1, for example, exhibit good activity with less than 20% residual attack, the compounds even inhibit root-knot formation almost completely (0–10% residual attack) in this test.

2.2 Action Against *Heterodera glycines* on Soybeans

Sandy soil is infested with eggs of the soybean cyst nematode *H. glycines*, approximately 6000 eggs per pot. The test compounds are then mixed in at the appropriate concentrations. The treated and infested soil is then put into 1c pots (180 ccm) and three soybeans (cv. Maple Arrow) are sown in each pot. Each treatment is repeated three times. The pots are incubated in a greenhouse at about 27° C. for four to five weeks. The plants are then carefully removed from the pots, the roots are washed, and the number of cysts is determined. The activity is rated in accordance with a scale of 1–9 (1 = full activity, 9 = no activity).

The compounds of Tables 1–4 exhibit good activity against *Heterodera glycines*, which is shown by the almost complete reduction of cyst formation.

We claim:

1. A 2-(Pyrimidyl or pyrazinyl)-imino-1,3-dithietane of formula I $$Ar-N=\underset{S}{\overset{S}{\diagup\!\!\!\diagdown}}\underset{X_2}{\overset{X_1}{\diagdown\!\!\!\diagup}} \quad (I)$$

wherein
Ar is one of the radicals

[four pyrimidinyl/pyrazinyl ring structures with $R_n$ substituents]

R is unsubstituted $C_1$–$C_3$alkyl or $C_1$–$C_3$alkyl which is substituted by halogen, $C_1$–$C_3$alkyl, $C_1$–$C_3$alkoxy, $C_1$–$C_3$alkylthio or cyano, independently of one another, or is unsubstituted or halo-substituted $C_3$–$C_7$alkenyl, unsubstituted or halo-substituted $C_3$–$C_7$alkynyl, or $C_3$–$C_5$cycloalkyl, $C_1$–$C_3$alkoxy, $C_1$–$C_3$alkylthio, di-$C_1$–$C_3$alkylamino, nitro or halogen, n is a number from 0 to 3, $X_1$ and $X_2$ independently of each other are hydrogen or halogen, including the addition salts formed with acids of the formula $H^{\oplus}X^{\ominus}$ in which the anion $X^{\ominus}$ is $Cl^{\ominus}$, $Br^{\ominus}$, $I^{\ominus}$, $HSO_4^-$, $H_2PO_4^-$, $H_2PO_3^-$, $NO_3^-$, $CH_3COO^{\ominus}$, $CH_2ClCOO^-$, $CF_3COO^-$, $HOCH_2COO^-$, $CH_3CH(OH)COO^{\ominus}$, $HOOCCOO^{\ominus}$, $HOOCCH_2COO^{\ominus}$, $HOOCCH=CHCOO^{\ominus}$,

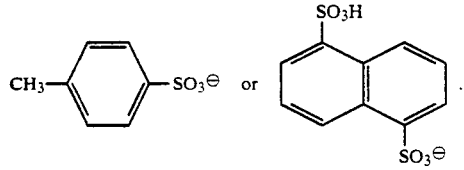

2. A compound according to claim 1, wherein R is methyl, methoxy, methylthio or chlorine, n is a number from 0 to 2, and $X_1$ and $X_2$ independently of each other are hydrogen or fluorine.

3. A compound according to claim 2, wherein R is methyl, methoxy or methylthio, n is 0 or 1, and $X_1$ and $X_2$ are hydrogen.

4. A compound of formula Ia

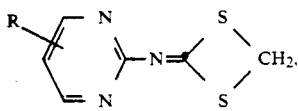

according to claim 3.

5. 2-(2-Pyrimidyl)-imino-1,3-dithietane according to claim 4.

6. A compound of formula Ib

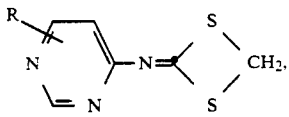

according to claim 3.

7. 2-(4-Pyrimidyl)-imino-1,3-dithietane according to claim 6.

8. A compound of formula Ic

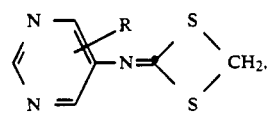

according to claim 3.

9. 2-(5-Pyrimidyl)-imino-1,3-dithietane according to claim 8.

10. A compound of formula Id

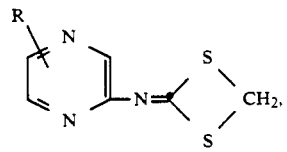

according to claim 3.

11. 2-(2-Pyrazinyl)-imino-1,3-dithietane according to claim 10.

12. A pesticidal composition for controlling or preventing an attack on plants by nematodes and fungi, which contains as active ingredient at least one compound of formula I according to claim 1.

13. A method of controlling or preventing an attack on cultivated plants by nematodes and fungi, which comprises applying an effective amount of a compound of formula I according to claim 1 to the plant or to the locus thereof.

14. The use of compounds of formula I according to claim 1 for controlling and/or preventing an attack on plants by nematodes and fungi.

* * * * *